US008038638B2

(12) United States Patent  (10) Patent No.: US 8,038,638 B2
Roberts et al.  (45) Date of Patent: Oct. 18, 2011

(54) PLASMA DETOXIFICATION AND VOLUME CONTROL SYSTEM AND METHODS OF USE

(75) Inventors: Craig P. Roberts, Carlsbad, CA (US); Ken Litzie, Tustin, CA (US)

(73) Assignee: Hemolife Medical, Inc., San Clemente, CA (US)

( * ) Notice: Subject to any disclaimer, the term of this patent is extended or adjusted under 35 U.S.C. 154(b) by 609 days.

(21) Appl. No.: 11/695,584

(22) Filed: Apr. 2, 2007

(65) Prior Publication Data
US 2007/0181499 A1  Aug. 9, 2007

Related U.S. Application Data

(63) Continuation-in-part of application No. 11/157,344, filed on Jun. 20, 2005, now abandoned, and a continuation-in-part of application No. 10/785,215, filed on Feb. 23, 2004, now abandoned.

(60) Provisional application No. 60/581,922, filed on Jun. 21, 2004.

(51) Int. Cl.
*A61M 1/34* (2006.01)
*B01D 61/14* (2006.01)
*B01D 61/18* (2006.01)
*B01D 24/00* (2006.01)
*B01D 29/00* (2006.01)
*B01D 37/00* (2006.01)
*B01D 15/00* (2006.01)

(52) U.S. Cl. ....... 604/5.04; 210/201; 210/203; 210/295; 210/435; 210/500.34; 210/500.35; 210/503; 210/645; 210/646; 210/660; 210/679; 604/4.01; 604/5.01

(58) Field of Classification Search .................. 210/201, 210/203, 295, 435, 500.34, 500.35, 502.1, 210/503, 645, 646, 660, 679; 604/4.01, 5.01, 604/5.04; 424/78.1, 140.1
See application file for complete search history.

(56) References Cited

U.S. PATENT DOCUMENTS
3,442,819 A * 5/1969 Herbert .................. 502/403
3,725,113 A   4/1973 Chang
(Continued)

FOREIGN PATENT DOCUMENTS
DE   31 10128 A1   9/1982
(Continued)

OTHER PUBLICATIONS

Anand, A.C., "Early Indicators of Prognosis in Fulminant Hepatic Failure: An Assessment of the King's Criteria", J. Hepatology, 1997, vol. 26, pp. 62-66.

(Continued)

*Primary Examiner* — John Kim
(74) *Attorney, Agent, or Firm* — K&L Gates LLP; Louis C. Cullman; Michelle Glasky Bergman

(57) ABSTRACT

An extracorporeal circuit for removing toxins from the blood and plasma volume control in patients suffering from sepsis and renal failure. The extracorporeal circuit disclosed herein comprises a plasma filter, a toxin removal device and optionally a hemofilter that minimizes electrolyte and protein depletion from the treated plasma while effectively removing both free and protein-bound toxins. The toxin removal device comprises adsorbent materials selected from the group consisting of activated carbon, ion exchange resins and non-ionic exchange resins and the adsorbent materials are coated with albumin. Also provided are associated methods for treating patients suffering from sepsis and renal failure using the disclosed extracorporeal circuit and toxin removal device.

21 Claims, 9 Drawing Sheets

U.S. PATENT DOCUMENTS

| | | | |
|---|---|---|---|
| 4,127,481 A | 11/1978 | Malchesky et al. | |
| 4,209,392 A | 6/1980 | Wallace | |
| 4,231,871 A | 11/1980 | Lipps et al. | |
| 4,267,047 A | 5/1981 | Henne et al. | |
| 4,269,706 A | 5/1981 | Sondermann | |
| 4,617,115 A | 10/1986 | Vantard | |
| 4,747,822 A | 5/1988 | Peabody | |
| 4,769,037 A | 9/1988 | Midcalf | |
| 4,988,569 A | 1/1991 | Okazaki et al. | |
| 5,015,388 A | 5/1991 | Pusineri et al. | |
| 5,091,091 A | 2/1992 | Terman | |
| 5,108,612 A | 4/1992 | Flaig et al. | |
| 5,194,157 A * | 3/1993 | Ghezzi et al. | 210/646 |
| 5,232,843 A * | 8/1993 | Bosley et al. | 435/135 |
| 5,240,601 A | 8/1993 | Mazid | |
| 5,571,418 A | 11/1996 | Lee et al. | |
| 5,679,260 A | 10/1997 | Boos et al. | |
| 5,744,042 A * | 4/1998 | Stange et al. | 210/645 |
| 6,287,516 B1 | 9/2001 | Matson et al. | |
| 6,730,266 B2 | 5/2004 | Matson et al. | |
| 6,736,972 B1 | 5/2004 | Matson | |
| 6,787,040 B2 | 9/2004 | Radunsky et al. | |
| 2004/0173530 A1 | 9/2004 | Radunsky et al. | |
| 2004/0228829 A1 | 11/2004 | Roberts et al. | |
| 2005/0169889 A1* | 8/2005 | Buasen et al. | 424/93.2 |

FOREIGN PATENT DOCUMENTS

| | | |
|---|---|---|
| EP | 0 787 500 A1 | 8/1997 |
| WO | 00/02603 A2 | 1/2000 |
| WO | 03/009885 A2 | 2/2003 |

OTHER PUBLICATIONS

Ash, S.R., "Treatment of Acute Hepatic Failure with Encepthalopahy: A Review", Int., J. Artif. Organs, 1991, vol. 14, pp. 191-195.

Awad, S.S., et al., "A Novel Stable Reproducible Model of Hepatic Failure in Canines", Journal of surgical Research, 2000, vol. 94, pp. 167-171.

Bende, S. et al., "Elimination of Endotoxin from the Blood by Extracorporeal Activated Charcoal Hemoperfusion in Experimental Canine Endotoxin Shock", Circulatory Shock, 1986, vol. 19, pp. 239-244.

Ellis, A.J., et al., "Temporary Extracorporeal Liver Support for Severe Acute Alcoholic Hepatitis Using the BioLogic-DT", Int. J. Artif. Organs, 1999, vol. 22, pp. 27-34.

Falkenhagen, D. et al., "Fractionated Plasma Separation and Adsorption System: A Novel System for Blood Purification to Remove Albumin Bound Substances", Artif. Organs, 1999, vol. 23, pp. 81-86.

Hughes, R. et al., "Use of Sorbent Columns and Haemofiltration in Fulminant Hepatic Failure", Bolld, Purif., 1993, vol. 11, pp. 163-169.

Hughes, R.D., et al., "Artificial Liver Support in Acute Liver Failure: A Review of Studies at King's", Artif. Organs, 1992, vol. 16, pp. 167-170.

Hughes, R.D., et al., "In-Vitro Blood Compatibility Studies on a New Polymer-Coated Charcoal for Haemoperfusion", The International Journal of Artificial Organs, 1980, vol. 3, No. 5, pp. 277-279.

Hughes, R.D., et al., "Platelet Function during Haemoperfusion in Acute Liver Failure", The International Journal of Artificial Organs, 1980, vol. 3, No. 1, pp. 30-34.

Kellum, J. A., et al., "Effect of Hemofiltration Filter Adsorption on circulating IL-6 Levels in Septic Rats", Critical Care, 2002, vol. 6, pp. 429-433.

Makin, A.J., et al., "Systemic and Hepatic Hemodynamic Changes in Acute Liver Injury", The American Physiological Societey, 1997, vol. 272, pp. G617-G625.

Morimoto, T., et al., "Plasma Adsorption Using Bilirubin-Adsorbent Materials as a Treatment for Patients with Hepatic Failure", Artificial Organs, 1989, pp. 447-452.

Mullen, K., et al., "Hepatic Encephalopahy", Schiff's Diseases of the Liver, Eighth-Edition, Lippincot-Raven Publishers, Philadelphia, 1999, pp. 545-581.

Nagaki, M., et al., "In Vitro Plasma Perfusion Through Adsorbents and Plasma Ultrafiltration to Remove Endotoxin and Cytokines", Circulatory Shock, 1992, vol. 38, pp. 182-188.

Nagaki, M., et al., "Removal of Endotoxin and Cytokines by Adsorbents and the Effect of Plasma Protein Binding", Liver Unit, King's College School of Medicine and Dentistry, 1991, vol. 4 pp. 43-50.

Nakae, H., et al., "Effectiveness of Combining Plasma Exchange and Continuous Hemodiafiltration (Combined Modality Therapy in a Parallel Circuit) in the Treatment of Patients wit Acute Hepatic Failure", Therapeutic Apheresis, 2001, vol. 5, No. 6, pp. 471-475.

Odnopozov, V. A., "Effect of Hemocarboperfusion on Organ Blood Flow and Survival in Porcine Endotoxic Shock", Critical Care Med., 1996, vol. 24, No. 12, pp. 2020-2026.

Peltekian, K. et al., "Role of Cytokines and Immune Mechanisms in Acute Liver Failure", Edited by Lee WM et al,, (eds), Cambridge Press, 1997, pp. 67-78.

Rahman, T.M., et al., "Review Article: Liver Support Systems in Acute Hepatic Failure", Aliment Pharmacol Ther, 1999, vol. 13, pp. 1255-1272.

Ronco, C., et al., "A Pilot Study of Coupled Plasma Filtration with Adsorption in Septic Shock", Critical Care Med. 2002, vol. 30, No. 6, pp. 1250-1255.

Ryan, C.J., et al., "Preclinical Evaluation of Haemoorbents", The International Journal of Artificial Organs, 1986, vol. 9, No. 5, pp. 293-296.

Ryan, C.J., et al., "Repeated Membrane Plasma Separation wit On-Line Sorbent Treatment of Plasma in the Conscious Rat", Artificial Organs, 1986, vol. 10, No. 2, pp. 135-144.

Schiodt, F.V., et al., "Etiology and Outcome for 295 Patients with Acute Liver Failure in the United States", Liver Transplantation and Surgery, vol. 5, No. 1 , Jan. 1999, pp. 29-34.

Schodt, F.V., et al., "Acetaminophen Toxicity in an Urban County Hospital", The New England Journal of Medicine, Oct. 16, 1997, vol. 337, No. 16, pp. 1112-1117.

Strange, J. et al., "Liver Support by Extracorporeal Blood Purification—A Clinical Observation", German Ministry for Research and Technology, Germany, 2000, vol. 6, No. 5, pp, 603-613.

Sudan, D.L., et al., "Long-Term Follow-up of Auxiliary Orthotopic Liver Transplantation for the Treatment of Fulminant Hepatic Failure", Surgery, 1997, vol. 122, No. 4, pp. 777-778.

Sussman, N.L., et al., "Reversal of Fulminant Hepatic Failure Using an Extracorporeal Liver Assist Device", Hepatology, 1992, vol. 16, No. 1, pp. 60-65.

Terblanche, J. et al., "Animal Models of Fulminant Hepatic Failure", Digestive Diseases and Sciences, 1991, vol. 26, No. 6, pp. 770-774.

Tetta, C., et al., "Endotoxin and Cytokine Removal in Sepsis", Ther. Apher., 2002, vol. 6, No. 2, pp. 109-115.

Wendon, J.A., et al., "Cerebral Blood Flow and Metabolism in Fulminant Liver Failure", Hepatology, 1994, vol. 19, pp. 1407-1413.

Wehler, M. et al., "Short-Term Prognosis in Critically Ill Patients with Cirrhosis Assessed by Prognostic Scoring Sytems", Hepatology, 2001, vol. 34, pp. 255-261.

Williams, R., "New Directions in Acute Liver Failure", Journal of the Regal College of Physicians of London, 1994, vol. 28, No. 6, pp. 552-559.

Venkataraman, R., et al., "Clinical Review: Extracorporeal Blood Purification in Severe Sepsis", Critical Care, 2003, vol. 7, No. 2, pp. 139-145.

Angus, D.C., et al., "Epidemiology of Severe Sepsis in the United States; Analysis of Incidence, Outcome, and Associated Costs of Care", Critical Care Med., 2001, vol. 29, No. 7, pp. 1303-1310.

Atti, M., et al., "Contact-Phase Activation During Hemodiafiltration Using the HFR Technique can be Confirmed with Some Types of Activated Carbon", Italian Journal of Nephrology, 2004, vol. 21, Suppl. 20, pp. S61-S66.

Martin, G.S., et al., "The Epidemiology of Sepsis in the United States from 1979 through 2000", The New England Journal of Medicine, 2003, vol. 348, 1546-1554.

* cited by examiner

PLASMA DETOXIFICATION AND VOLUME CONTROL SYSTEM AND METHODS OF USE

RELATED APPLICATIONS

This application is a continuation-in-part of U.S. patent application Ser. No. 11/157,344 filed Jun. 20, 2005, now abandoned, which claims priority under 35 U.S.C. §119(e) to U.S. Provisional Patent Application Ser. No. 60/581,922 filed Jun. 21, 2004 and which is a continuation-in-part of U.S. patent application Ser. No. 10/785,215 filed Feb. 23, 2004, now abandoned, the entire contents of which are incorporated by reference herein in their entirety.

FIELD OF THE INVENTION

The present invention related to devices and associated methods for plasma detoxification. Specifically, the present invention relates to an extracorporeal system that uses an adsorption column containing activated charcoal and ionic and non-ionic resins in combination with a hemofilter to remove toxins associated with sepsis and renal failure, treat chronic metabolic acidosis and control patient plasma water without the use of a renal dialyzer or dialysate.

BACKGROUND OF THE INVENTION

Despite advances in supportive care, septic shock remains a major cause of morbidity and mortality. In 1995, there were an estimated more than 750,000 cases of sepsis in the United States, of whom 383,000 (51.1%) received intensive care and an additional 130,000 (17.3%) were ventilated in an intermediate care unit or cared for in a coronary care unit (Angus D C et al. Epidemiology of severe sepsis in the United States: Analysis of incidence, outcome, and associated costs of care. Crit Care Med 2001; 29:1303-10). Mortality was more than 28% or 215,000 annually. The incidence and mortality of sepsis increase with age. Sepsis is the second leading cause of death in among patients in non-coronary intensive care units and the $10^{th}$ leading cause of death overall in the United States (Martin G S et al. The epidemiology of sepsis in the United States from 1979 through 2000. N Eng J Med 2003; 348: 1546-54). Furthermore, sepsis substantially reduces the quality of life of those who survive. Care of patients with sepsis costs an average of $22,000 per patient resulting in an economic burden of nearly $17 billion annually in the United States alone.

Sepsis generally develops as a result of the host response to infection. The pathogenesis of sepsis represents a complex constellation of interconnected events. Sepsis is a form of severe systemic inflammation due to local and systemic effects of circulating pro-inflammatory mediators. With the identification of the systemic inflammatory response as a major component in the pathogenesis of the septic shock syndrome, much of the recent work has focused on modulating this response. This includes anti-endotoxin therapies in patients with Gram-negative sepsis and therapies to modulate the pro-inflammatory mediators produced in response to infection, such as TNF-alpha, platelet-activating factor and complement. High-flow hemofiltration has the potential advantage of clearing both endotoxin and pro-inflammatory mediators. The bacterial toxins generated by the infecting organisms trigger complex immunologic reactions. A large number of mediators, including tumor necrosis factor, leukotrienes, lipoxygenase, histamine, bradykinin, serotonin and interleukin-2, have been implicated in addition to endotoxin (the lipid fraction of the lipopolysaccharides released from the cell wall of gram-negative enteric bacilli). Presently, the only recommended therapeutic approach remains close microbiological surveillance. Prophylactic antibiotics and enteral decontamination have only a minor role: they may have an adverse effect by the selection of multiple resistant strains. (Ronco C et al. A pilot study of coupled plasma filtration with adsorption in septic shock. Crit Care Med 2002; 30:1250-55).

The scientific literature provides some interesting experimental alternatives for treating sepsis. See for example J. A. Kellum and M. K. Dishart. Effect of Hemofiltration Filter Adsorption on Circulating IL-6 Levels in Spectic Rats. Critical Care 2002, 6:429-433 (hereinafter "Kellum"). Kellum discloses using a hydrogel-type membrane made from an acrylonitrile and sodium methallyl sulfonate copolymer to remove IL-6 from the blood of septic rats. Reduction in overall IL-6 levels was noted, however, the filter used has a limited absorption profile and not all sepsis-associated cytokines are removed.

However, many cytokines and other toxins are bound to the blood protein albumin. Conventional dialysis membranes do not remove substantial quantities of these protein-bound toxins from the blood because protein-impermeable membranes are generally used. Consequently, other extracorporeal circuits such as continuous renal replacement therapies (CRRT), coupled plasma filtration adsorption (CPFA) and continuous veno-venous hemodiafiltration (CVVHDF) may help minimize cell-associated cytokine concentrations in the blood of septic patents. See for example C. Tetta et al. Endotoxin and Cytokine Removal in Sepsis. Ther. Apher. 2002. 6:109-115. (hereinafter "Tetta"). Tetta concluded that CPFA may be preferable to CRRT and CVVHDF for treating septic patents, but that much clinical research was need to prove efficacy. These more invasive detoxification methods enable higher clearance of protein-bound toxins due to direct contact between the sorbent and the albumin/toxin-complex.

Continuous veno-venous hemofiltration (CVVH) was designed as a renal replacement therapy for patients with acute renal failure. In hemofiltration the blood is forced through a semipermeable membrane and water and small molecules are filtered out of the blood. Hemofiltration is slower and less physiologically disturbing than hemodialysis, it is often chosen over intermittent hemodialysis when blood pressure instability is a problem and CVVH is generally more efficient than peritoneal dialysis. In some intensive care units the use of CVVH is increasing as appreciation builds for its utility in the management of non-oliguric patients, in particular those with multiple organ dysfunction or failure, when their treatment includes very large amounts of intravenous fluids. And finally, experimental work is focusing on the possible role of CVVH as an adjunct in the treatment of the sepsis syndrome.

Healthy kidneys regulate the body's internal environment of water and salts and excrete the end products of the body's metabolic activities and excess water (urine). They also produce and release into the bloodstream hormones that regulate vital functions including blood pressure, red blood cell production, and calcium and phosphorus metabolism. Impaired kidney function may affect any or all of these processes and may be due to problems in the kidney, a disease in other organs, or caused by normal, age-related processes. It may be acute or chronic and either minor or life threatening. All of these distinctions are important determinants of prognosis and appropriate treatment. When a person's loss of kidney function is so severe as to be incompatible with life, the person is said to be in renal failure.

Acute Renal Failure (ARF) is a syndrome with multiple causes; its associated consequences affect all organ systems. Defined as a sudden loss of renal function (over several hours to several days), ARF results in derangements in extracellular fluid balance, acid base, electrolytes and divalent cation regulation. An increased serum creatinine concentration, accumulation of other nitrogen-based waste products, and often a decline in urinary output are the hallmarks of ARF.

Although many advances in organ support technologies have occurred during the past two decades, the absolute mortality rates for ARF acquired in the hospital and in the intensive care unit are approximately 45% and 70%, respectively (Thadhani R et al., Acute renal failure, N Engl J Med. 334: 1448-60, 1996). However the demographics of ARF have changed, with patients generally being older and having a higher acuity of illness. Fortunately, renal function recovery (ability to discontinue dialysis) in the past 20 years has remained greater than 50-75% in survivors of ARF.

More than 20 definitions of ARF have been published to date. Despite the difficulty in defining the syndrome, ARF occurs in approximately 1% of hospitalized patients, in as many as 20% of patients treated in ICUs and as many as 4-15% of patients after cardiovascular surgery. Approximately 30% of patients who experience ARF will require renal replacement therapy (peritoneal dialysis, intermittent hemodialysis or continuous hemofiltration). Community-acquired ARF occurs in approximately 209 patients per one million population, and the frequency of this syndrome is increasing in hospitalized patients (Liano F et al., Epidemiology of acute renal failure: a prospective, multicenter, community-based study, Kidney Int. 50:811-8, 1996).

More than 50 identified pathophysiologic pathways are responsible for ARF. Traditionally, the evaluation of ARF has focused on the determination of whether the cause of renal failure is pre-renal (60% of community-acquired ARF, a condition resulting in decreased "effective renal perfusion"), post-renal (5-15% of community-acquired ARF, an obstruction to urinary outflow) or intrinsic renal (due to pathophysiologic derangements in the renal tubules, interstitium, vasculature or glomeruli; includes acute tubular necrosis, the most common cause of ARF in hospitalized patients) (Albright R C Jr. et al., Acute renal failure: a practical update, Mayo Clin Proc. 76:67-74, 2001).

Therapy to correct the pathophysiological impairments of ARF can be either nondialytic or dialytic in nature. Nondialytic therapy is focused on insuring that renal perfusion is maximized and correcting impairments. A variety of growth factors, hormones and drugs are currently under evaluation as nondialytic therapy for ARF. Dialytic therapy consists of peritoneal dialysis, intermittent hemodialysis or continuous hemofiltration.

Renal dialysis is an artificial method of maintaining the chemical balance of the blood when the kidneys have failed. The term dialysis refers to the process in which soluble waste products are separated from the blood using a semipermeable membrane. The blood is cleansed of impurities by cycling the blood through a machine containing a hemodialyzer membrane. On the other side of the membrane is a solution comprised of specific components that extract the impurities from the patient's blood. This solution is called the dialysate. Blood is both removed and returned to the patient via catheters. The effectiveness of dialysis depends on both its duration and efficiency.

Peritoneal dialysis, in contrast to hemodialysis, which cleanses the blood outside the body, works inside the body using the peritoneal membrane as the semipermeable barrier through which the blood can be filtered. The dialysate is infused directly into the patient's peritoneal cavity through a catheter; the cavity is used as a reservoir for the dialysate. Toxins in the blood filter through the peritoneal membrane into the cleansing solution, which is then withdrawn from the body through the same catheter and discarded. This procedure can be self-administered by patients several times a day.

Hemodialysis allows the extracorporeal removal of water and solutes from the blood by diffusion across a concentration gradient. Blood is pumped along one side of a semi-permeable membrane and a crystalloid solution is pumped in the opposite direction on the other side of the membrane. Solutes of very small molecular weight diffuse across the membrane in an attempt to equilibrate their concentrations. The pore size in the semi-permeable membrane determines its utility in ultrafiltration. Ultrafiltration membranes that are utilized in hemofilters allow the passage of molecules with a molecular weight of less than 20,000 Daltons. Thus ions and small chemicals present in plasma are filtered freely, including sodium, potassium, phosphate, bicarbonate, glucose and ammonia. So are larger soluble endogenous substances such as myoglobin, insulin, and interleukins, and certain exogenous substances circulating in plasma, including medications (vancomycin, heparin) and toxins (endotoxin, pesticides). Molecules that are bound to plasma proteins would not be filtered effectively by an ultrafiltration membrane.

Many side effects of hemodialysis are caused by rapid changes in the body's water and electrolyte balance during dialysis. These include muscle cramps, hypotension, complement activation and leukopenia. In addition patients undergoing peritoneal dialysis run the risk of serious peritoneal infections, some of which can progress to septic shock.

Extracorporeal circuits are well known in the prior art. However, the known extracorporeal circuits are used primarily as artificial kidneys and perfusion devices. Perfusion devices are primarily used to provide circulatory assistance after open heart surgery. Kidney diafiltration, dialysis and pure hemofiltration are processes used to replace the function of the failing or diseased kidney. These devices principally rely on semi-permeable membrane technology and the principles of osmotic diffusion to remove proteins, salts and urea from the blood. Additionally, kidney dialysis can be combined with ultrafiltration to remove excess fluid from the blood or be combined with substitution infusion fluid to replace fluids and salts lost in the hemodiafiltration process. However, extracorporeal circuits used to augment and/or replace diseased kidneys are not designed to remove the complex biological toxins the liver is responsible for.

U.S. Pat. No. 6,186,146 B1 (hereinafter "the '146 patent") issued Feb. 13, 2001 to Glickman discloses an extracorporeal circuit having a filter device incorporated therein. Specifically, the '146 patent describes a treatment for cancer where cytotoxic drugs and biological agents are infused directly into a diseased organ. The patent's blood, leaving the treated organ, is diverted via an extracorporeal circuit wherein the cytotoxic and/or biological agent is removed from the blood via an inline filter before reaching the general circulation. No details as to the filter's composition are provided. However, the simple extracorporeal circuit disclosed in the '146 patent is intended to remove a defined concentration of a specific known chemotherapeutic and/or biological agent. It is not intended as a general replacement for a diseased organ. Moreover, no details are provided as to how one of ordinary skill in the art would use the disclosed device to remove other biological toxins.

Consequently, there remains a need for extracorporeal devices and methods that can be used to safely remove toxins from plasma in patients suffering from sepsis. Additionally, there remains a recognized need for extracorporeal devices and methods useful for removing toxins and balancing plasma water in patients with acute renal disease.

SUMMARY OF THE INVENTION

The present invention describes an extracorporeal plasma detoxification system that can remove toxins associated with and resulting from sepsis, liver failure and renal failure and correct electrolyte imbalance, treat chronic metabolic acidosis and control patient plasma water in patients in renal failure without the use of a renal dialyzer or dialysate. The present invention comprises an adsorptive toxin removal device with an optional hemofilter to effectively detoxify human plasma and balance blood volume in patients suffering from sepsis, liver failure and renal failure.

In one embodiment of the present invention, an extracorporeal system is provided for the removal of cytokines and toxins from plasma and to enable the balance of plasma water, the system comprising a plasma filter for separating plasma from blood, and an adsorption device for removing cytokines and toxins from the plasma; wherein the adsorption device comprises two or more adsorbents selected from the group consisting of activated carbon, non-ionic exchange resin and ion exchange resin and wherein the adsorbents are coated with albumin prior to use.

In another embodiment, the plasma filter has a molecular weight cutoff greater than 0.2 microns. In another embodiment, the albumin coating does not additionally contain a semi-permeable membrane.

In another embodiment of the present invention, the extracorporeal system further comprises a hemofilter for removing small molecules from the plasma and balancing plasma water.

In another embodiment, the activated carbon comprises uncoated coconut shell granule charcoal, uncoated organic granule charcoal or uncoated synthetic carbon. In another embodiment, the adsorbent is at least one ionic exchange resin.

In another embodiment, the adsorbent is at least one non-ionic exchange resin selected from the group consisting of non-ionic aliphatic ester resins, non-ionic polystyrene divinyl benzene resins and other non-biologic adsorptive resins. In yet another embodiment, at least one of said non-ionic aliphatic ester resins has an average surface area of approximately 500 $m^2/g$ and an average pore size of approximately 450 Angstroms and a mean particle diameter of 560 μm. In another embodiment, at least one of said non-ionic polystyrene divinyl benzene resins has an average surface area of approximately 700 $m^2/g$ with an average pore size of 300 Angstroms and a mean particle diameter from approximately 35 μm to approximately 120 μm. In another embodiment, at least one of said non-ionic polystyrene divinyl benzene resins has an average surface area of approximately 600 $m^2/g$ with an average pore size of 300 Angstroms and a mean particle diameter from approximately 300 μm to approximately 500 μm.

In another embodiment of the present invention, the extracorporeal system further comprises at least one particle filter downstream of the adsorption device in the extracorporeal system.

In another embodiment, the albumin coating consists essentially of albumin and a physiologic solution. In another embodiment, the albumin is human albumin.

In one embodiment of the present invention, an extracorporeal system for the removal of cytokines and toxins from plasma and to enable the balance of plasma water comprising: a plasma filter for separating plasma from blood, and an adsorption device for removing cytokines and toxins from the plasma; wherein the adsorption device comprises two or more adsorbents selected from the group consisting of activated carbon, non-ionic exchange resin and ion exchange resin and wherein the adsorbents are coated with albumin prior to use, the albumin coating consisting essentially of albumin and a physiologic solution.

In another embodiment of the present invention, a method is provided for removing toxins from blood comprising: circulating the venous blood of a patient through an extracorporeal circuit having an adsorptive toxin removal device disposed therein wherein the toxin removal device comprises activated carbon and two or more non-ionic resins wherein the activated carbon and the two or more non-ionic resins are coated with albumin. In another embodiment, the method further comprises the step of circulating the detoxified blood through a hemofilter.

In yet another embodiment of the present invention, a method is provided for treating a disease or disorder in a mammal comprising: circulating the venous blood of a patient through an extracorporeal circuit having an adsorptive toxin removal device disposed therein wherein the adsorptive toxin removal device comprises activated carbon and two or more non-ionic resins wherein the activated carbon and the two or more non-ionic resins are coated with albumin, and wherein the extracorporeal circuit optionally further comprises a hemofilter.

In another embodiment, the disease or disorder is sepsis. In another embodiment, the disease or disorder is renal failure. In another embodiment, the disease or disorder is liver failure.

DEFINITION OF TERMS

Figure 1:
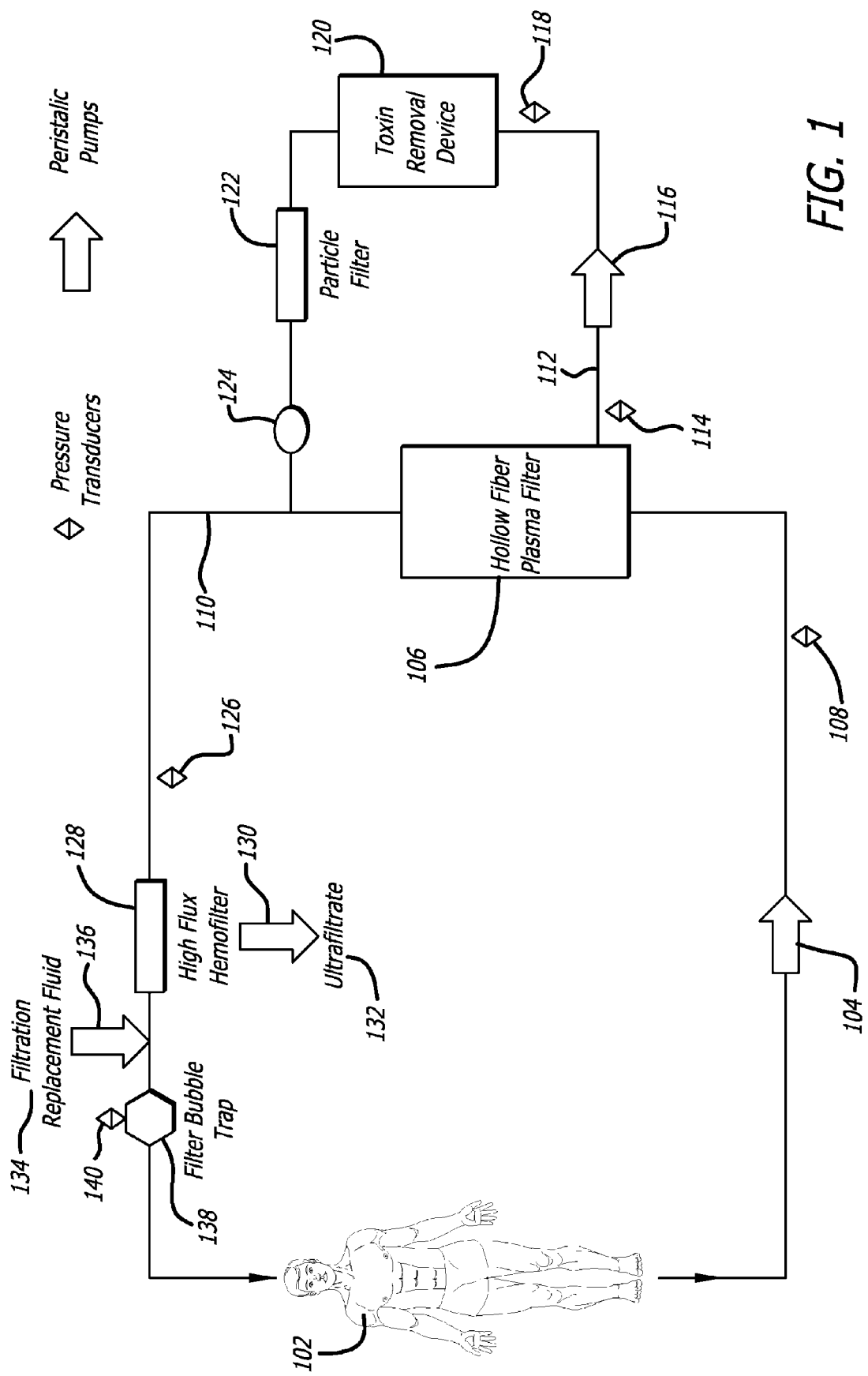
FIG. 1 is a schematic diagram of an embodiment of the extracorporeal plasma detoxification system of the present invention.

The following definition of terms is provided as a helpful reference for the reader. The terms used in this patent have specific meanings as they related to the present invention. Every effort has been made to use terms according to their ordinary and common meaning. However, where a discrepancy exists between the common ordinary meaning and the following definitions, these definitions supercede common usage.

Absorbent: As used herein "absorbent" refers to a medium such as activated carbon, an ionic or a non-ionic resin that retains a biologically active organic molecule or inorganic salt. Generally, absorbent refers to something that absorbs. Absorption is the taking in by chemical or molecular attraction similar to how water is taken in and held by a sponge.

Adsorbent: As used herein "adsorbent" refers to a medium such as activated carbon, an ionic or a non-ionic resin that retains a biologically active organic molecule or inorganic salt. Generally, adsorbent refers to something that adsorbs. Adsorption is the taking up and holding by chemical attraction to the surface of a solid substance similar to how a cloth may adsorb large dye molecules by holding them on the surface of the fibers by chemical attraction.

Exchange Resin: As used herein "exchange resin" generally refers to the ionic or non-ionic exchange resin component of the present invention. Furthermore it is understood that term exchange resin may be used collectively to refer to both ion exchange resins and non-ionic exchange resins in those embodiments where an exchange resin is added to the extracorporeal circuit in combination with the adsorptive toxin removal device of the present invention.

Toxin removal device: As used here "toxin removal device" refers to one or more cartridges or containers that contain one or more adsorbents or absorbents capable of removing organic molecules and/or inorganic salts from plasma or other biological fluids. The inventors believe that most ionic and non-ionic resins and activated charcoal act as adsorbents by attaching to their surface and retaining thereon organic molecules and inorganic salts. However, the present inventors do not wish to be bound by this theory. Therefore, for the purposes of this invention, the term "toxin removal device" will include materials that either adsorb or absorb molecules from the blood and/or plasma of patients.

Moreover, the term "toxin removal device" can mean a single unitary device wherein one or more toxin removing compounds are contained therein, either mixed or physically separated. However, the term "toxin removal device" can also refer to a plurality of discrete unitary devices each containing one or more separate toxin removal compositions. The discrete devices may be connected in series depending on the device design and application.

Toxin: As used herein "toxin" refers to any organic or inorganic compound that when present in a patient's blood above a tolerable threshold causes an adverse effect on the patient. Representative examples include, but are not limited to cytokines including interleukins, interferons, tumor necrosis factors alpha or gamma, soluble proteins, bilirubin, creatinine, amino acids, nucleic acids, bacterial toxins including endotoxins, exotoxins, lipopolysacccharides, cellular enzymes, bacterial cell wall components and pharmaceuticals such as acetaminophen.

DETAILED DESCRIPTION OF THE INVENTION

The present invention describes an extracorporeal plasma detoxification system that can remove toxins associated with sepsis, end-stage chronic liver disease, liver failure and renal failure and correct electrolyte imbalance, treat chronic metabolic acidosis and control patient plasma water in patients in renal failure without the use of a renal dialyzer or dialysate.

The present invention combines an adsorptive toxin removal device with an optional hemofilter to effectively detoxify human plasma and balance blood volume in patients suffering from sepsis, liver failure and renal failure.

The major danger associated with sepsis is septic shock caused by the release of endotoxin associated with bacterial cell walls. These toxins cause inflammatory responses by over-exciting the immune system. The immune response deals well with relatively minor invasions but such a massive overload can cause major shock in which the blood pressure falls dramatically. However, once sepsis has set in, treatments which kill the bacteria make the problem worse by causing the release of more bacterial endotoxin from the dying bacteria. Therefore sepsis is a life-threatening condition that until now was extremely difficult to treat or control.

Acute renal failure is defined as the sudden loss of kidney function (over several hours to days) resulting in derangement of extracellular fluid balance, acid base, electrolytes and divalent cation regulation. Additionally, increased serum creatinine concentration, accumulation of other nitrogen-based waste products and often a decline in urinary output are hallmarks of acute renal failure. Renal dialysis is required when the pathophysiologic derangements in electrolytes, fluid balance and waste levels reach undesirable levels. However, current renal dialysis technology does not address the needs of the patient in acute renal failure.

Sepsis is a life threatening complication associated with end-stage liver disease and acute liver failure (ALF), among other causes. While the exact anatomical and physiological parameters associated with sepsis are not entirely understood, it is generally believed that sepsis is caused by the loss of the liver's structural integrity that allows normal intestinal flora to invade the blood. Furthermore, sepsis is also associated with abdominal surgery and severe burns.

Consequently, the present inventors have developed an extracorporeal system useful for removing toxins from the plasma of patients suffering from sepsis and/or liver or renal failure. Additionally, the present invention will also remove toxins from the plasma, and plasma water, as well as balance electrolytes and water in the plasma of patients suffering from renal failure.

The present inventors have designed a system for detoxifying the plasma of patents in need thereof that obviates problems associated with biocompatibility, electrolyte imbalances and protein permeability associated with conventional hemofiltration/diafiltration systems. Thus, the present invention provides a blood toxin removal system that does not result in clinically significant electrolyte imbalances or excessive protein removal from the treated patients' plasma. However, the present inventors have retained the simplicity and clinical acceptability of the standard extracorporeal circuits commonly used for treating kidney failure and cardiopulmonary support. Thus it is possible to introduce the detoxifying extracorporal circuit of the present invention directly into conventional systems for continuous renal replacement therapy such as the B|BRAUN DIAPACT™ CRRT (see http://www.bbraun.com/for details).

One embodiment of the extracorporeal system of the present invention will be described generally with reference to FIG. 1. In FIG. 1 blood is aspirated from a patient 102 in need of plasma detoxification or plasma water balancing. Blood is aspirated from the large vein of a patient via one lumen of a conventional dual lumen catheter connected to a peristaltic pump 104 and directed into a plasma filter 106 where the blood cells are separated from the plasma fraction of the blood. A pressure transducer 108 is provided between peristaltic pump 104 and hollow fiber plasma filter 106 to assess the flow/pressure characteristics of the resistance components. In one embodiment of the present invention a suitable plasma filter is a hollow fiber filter having a total surface area of 1 square meter and a 0.45 µM cutoff provided by Minntech, Inc. (Minneapolis, Minn.). The separated blood leaves the hollow fiber plasma filter 106 and can continue in one of two pathways. Blood cells are returned to the patient via pathway 110 and the separated plasma enters pathway 112. The plasma is pulled across the semi-permeable membrane of the plasma filter 106 by peristaltic pump 116 and propelled through adsorption column 120, the toxin removal device of the present invention, which contains a mixture of adsorbent materials. The flow of plasma through pathway 112 is monitored by pressure transducers 114 and 118. The purpose of the adsorptive toxin removal device is to remove both protein-bound and soluble toxins. Leaving adsorbent column 120, the plasma flows through a particle filter 122 before being recombined with the patient's blood cells from pathway 110 at a connection between plasma filter 106 and hemofilter 128. In addition, an optional heat exchanger 124 in the extracorporeal circuit can assist in the maintenance of patient temperature.

In one embodiment of the present invention, blood leaving the plasma filter 106 combines with plasma leaving particle filter 122 then passes through pressure transducer 126 and enters a high flux (0.3 m², 55,000 Dalton fiber membrane permeability) hemofilter 128. The high flux hemofilter 128 allows for both the exchange of plasma water using a technique commonly referred to as zero balance ultrafiltration (ZBUF) and the removal of excess patient plasma water with a technique commonly referred to as continuous veno-venous hemofiltration (CVVH). The addition of a balanced electrolyte replacement solution (filtration replacement fluid) 134 utilized in the ZBUF technique is controlled by peristaltic pump 136. The removal of plasma water (ultrafiltrate) 132 in the CVVH technique is also controlled by peristaltic pump 130.

In the final step, extracorporeal air is removed by bubble trap 138 equipped with a pressure transducer 140 in the circuit before returning to patient 102.

Figure 2:
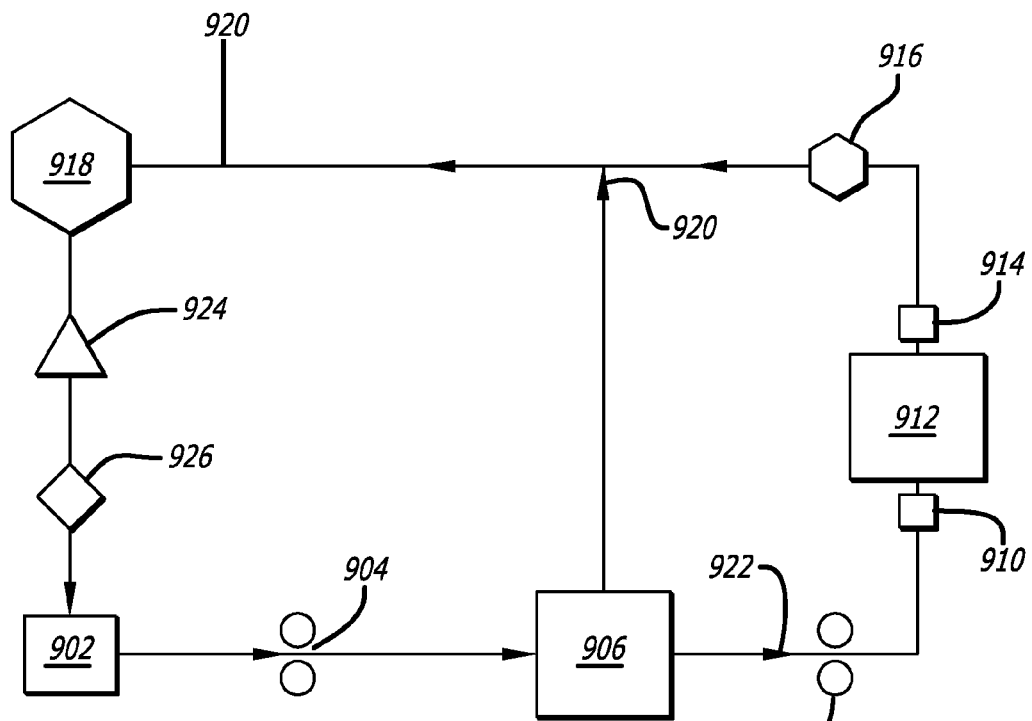
FIG. 2 is a schematic diagram showing one embodiment of the system of the present invention having a single toxin removal device.

Another embodiment of the present invention is depicted in FIG. 2. In FIG. 2 blood is aspirated from a patient 902 in need of plasma detoxification using a conventional dual lumen renal catheter connected to a peristaltic pump 904 and directed into a plasma filter 906 where the blood cells are separated from the plasma fraction of the blood. In one embodiment of the present invention, a suitable plasma filter 906 is a hollow fiber filter having a total surface are of 1 meter and a 0.45 µM cutoff is provided by Minntech, Inc. (Minneapolis, Minn. 55447). The separated blood leaves the hollow fiber plasma filter 906 by one of two routes. Blood cells are returned to the patent via pathway 920 and the separated plasma enters pathway 922. At pathway 922 the separated plasma moves into the toxin removal device of the present invention 912 (see also FIG. 5). The separated plasma may be assisted by optional pump 908 and may be optionally pre-filtered through pre-filter 910 prior to entering the toxin removal device 912. Next the detoxified plasma exits the toxin removal device 912 and optionally passes through a second pre-filter 914 before entering the particle filter 916. Pre-filters 910 and 914 may be composed of any one of different compounds including, but not limited to polypropoylene and generally have a pore size in the range of approximately 3 µM to 5 µM. The particle filter 916 may be composed of any biocompatible material and generally has a pore size that does not exceed 0.45 µM. The particle filter assures that and micro-particulates released by the upstream devices are removed from the detoxified plasma before being returned to the patient.

The detoxified plasma is returned to patient via pathway 920 where it rejoins the separated blood cells which together are pumped through a hemoconcentration filter 918 that removes excess fluid from the blood. The returning blood may then optionally be heated by heater 924 and then passes into bubble trap 926 before returning the patient 902.

Figure 3:
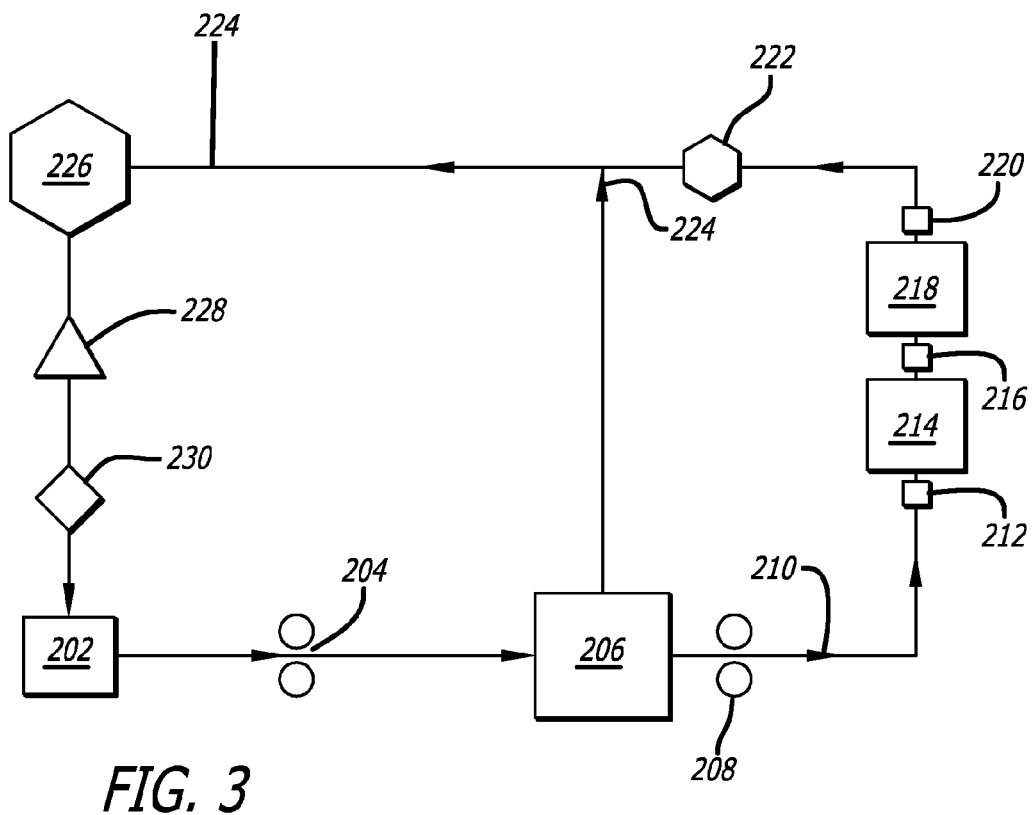
FIG. 3 is a schematic diagram showing another embodiment of the system of the present invention having a plurality of toxin removal devices in series.

FIG. 3 depicts another embodiment of methods for practicing the present invention. In FIG. 3, the process begins as blood is aspirated from a patient 202 in need of plasma detoxification using a conventional dual lumen renal catheter connected to a peristaltic pump 204 and directed into a plasma filter 206 where the blood cells are separated from the plasma fraction of the blood. The separated blood leaves the hollow fiber plasma filter 206 by one of two routes. Blood cells are returned to the patient via pathway 224 and the separated plasma enters pathway 210. At pathway 210 the separated plasma moves into the first toxin removal device of the present invention at 214. The separated plasma may be assisted by optional pump 208 and may be optionally pre-filtered through pre-filter 212 prior to entering the first toxin removal device 214. Next the partially detoxified plasma exits the first toxin removal device 214 and optionally passes through a second pre-filter 216 before entering a second toxin removal device 218. After passing through the second toxin removal device 218, the detoxified plasma may then optionally pass through a third pre-filter 220 before entering the dead-end filter 222. Pre-filters 212, 216 and 220 may be composed of any one of different compounds including, but not limited to polypropylene and generally have a pore size in the range of approximately 3 µM to 5 µM. The dead-end filter 222 may be composed of any biocompatible material and generally has a pore size that does not exceed 0.45 µM.

In one embodiment of the present invention, a suitable plasma separation filter is a hollow fiber filter having a total surface area of 1 meter and a cutoff between 0.2 and 0.45 µm. In another embodiment, a suitable plasma separation filter is a hollow fiber filter having a total surface area of 1 meter and a 0.45 µm cutoff and is provided by Minntech, Inc. (Minneapolis, Minn.).

The detoxified plasma is returned to patient via pathway 224 where it rejoins the separated blood cells and together is pumped through a hemoconcentration filter 226 that removes excess fluid from the blood. The returning blood may then optionally be heated by heater 228 and then passes into bubble trap 230 before returning the patient 202.

When multiple toxin removal devices are used as depicted in FIG. 3 it is not important which type of toxin removal device the plasma enters first. Moreover, the present inventors envision embodiments where the more than two toxin removal devices are attached in series, that is a plurality of toxin removal devices wherein a plurality denotes two or more such devices. In one embodiment of the present invention the first toxin removal device 214 comprises activated charcoal and the second toxin removal device 218 comprises one or more non-ionic resins. In another embodiment of the present invention the first toxin removal device 214 comprises one or more non-ionic resins and the second toxin removal device 218 comprises activated charcoal. In yet still another embodiment both toxin removal devices are the same and may contain both activated charcoal and/or non-ionic resins.

Furthermore, it is understood that substitution infusion fluids such as those used in renal dialysis may be added to the extracorporeal circuit of the present invention at one or more places in the process. For example, and not intended as a limitation, substitution infusion fluid may be added before the blood reaches the plasma filter. In another embodiment the substitution infusion fluid may be added before entering the hemofilter or hemoconcentration filter or at any point in between these two points in the circuit.

Figure 4:
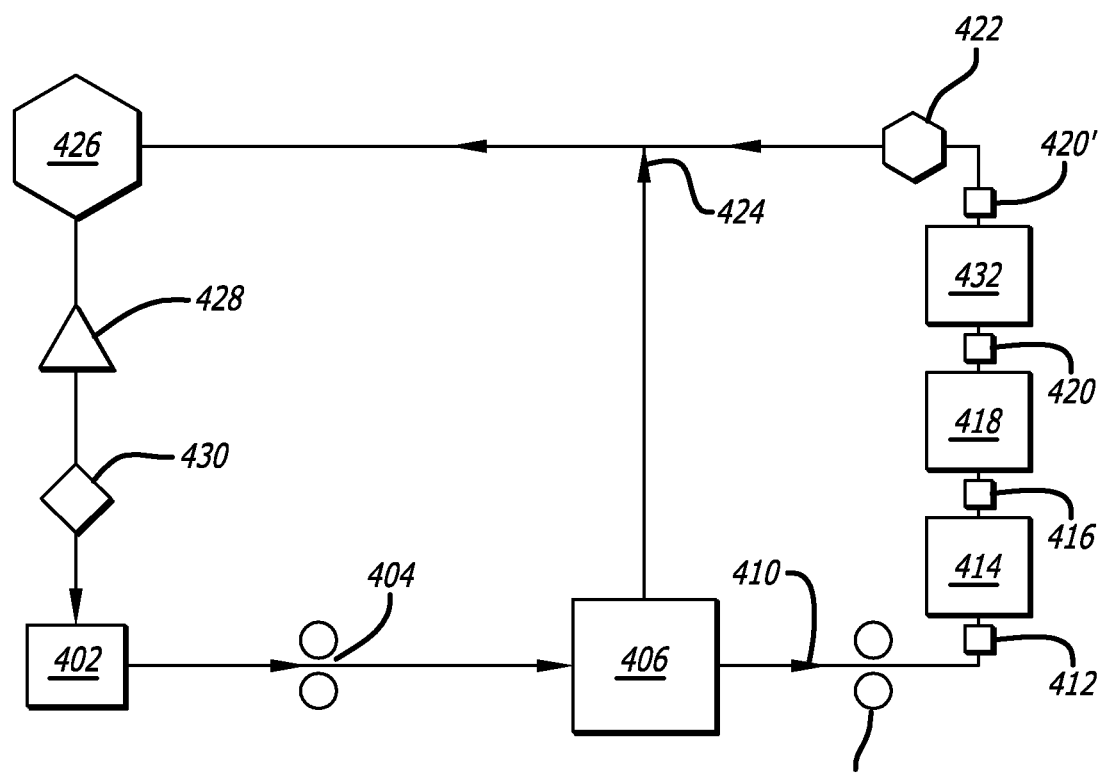
FIG. 4 is a schematic diagram showing another embodiment of the system of the present invention having a plurality of toxin removal devices in series.
Figure 5:
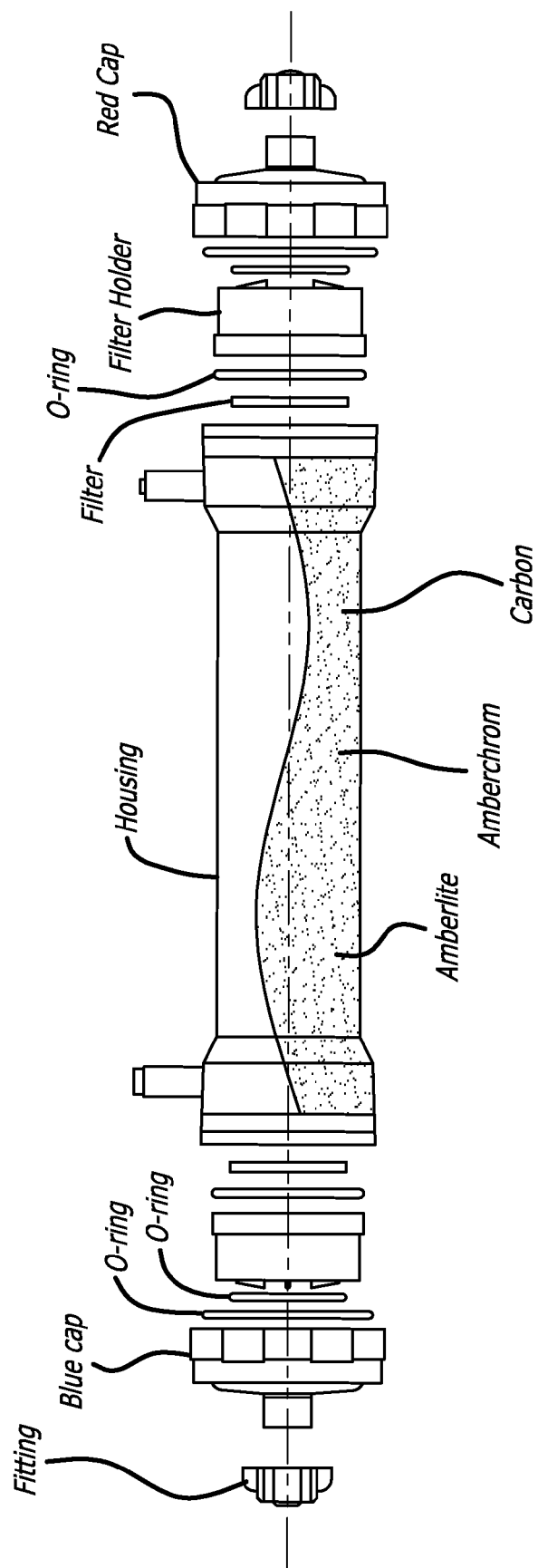
FIG. 5 depicts one embodiment of the adsorptive toxin removal device made in accordance with the teachings of the present invention.

FIG. 4 depicts an embodiment wherein the toxin removal device includes the additional feature of at least one ion exchange resin component 432 downstream (or alternatively upstream) of toxin removal devices connected in series 414 and 418 wherein the toxin removal devices 414 and 418 are charcoal and at least one non-ionic resin respectively (or visa versa). In an exemplary, non-limiting embodiment, the ion exchange resin of 432 is anion exchange resin, in another embodiment 432 is a cation exchange resin and in yet a third embodiment 432 is a mixed-bed ion exchange resin (cation mixed with an anion exchange resin). Reference number 434 is a pre-filter composed of any one of different compounds including, but not limited to polypropylene and generally has a pore size in the range of approximately 3 µM to 5 µM. In FIG. 5, reference numbers 402, 404, 406, 408, 410, 412, 416, 420, 422, 424, 426, 428 and 430 correspond to numbers 202, 204, 206, 208, 210, 212, 216, 220, 222, 224, 226, 228 and 230 in FIG. 3.

The adsorptive toxin removal device of the present invention is comprised of biologically active materials that adsorb (or absorb, see discussion supra) blood plasma-borne toxins that accumulate due to sepsis, or diminished liver or kidney function. The toxin removal device of the present invention may contain one or more material selected from the group consisting of activated charcoal and ion exchange resins. Essentially, ion exchange resins are classified as cation exchangers, which have positively charged mobile ions available for exchange and anion exchangers, whose exchangeable ions are negatively charged. Non-ionic exchange resins bind macromolecules via intermolecular forces, also referred to as van der Waal's forces, the weak attractive forces that hold non-polar molecules together (or non-polar regions of molecules having polar groups).

Both anion and cation exchange resins are produced from the same basic organic polymers. However, they differ in the ionizable group attached to the hydrocarbon network. It is this functional group that determines the chemical behavior of the resin. Ionic exchange resins can be broadly classified as strong or weak acid cation exchangers or strong or weak base anion exchangers. In an ion exchange process, cations or anions in a liquid solution (usually aqueous) replace dissimilar and displaceable ions of the same charge contained in the ion exchange resin.

Non-ionic exchange resins are particular advantageous when used in accordance with the teachings of the present invention because they are less prone to bind (and thus remove from the blood) essential cations and anions such as, but not limited to, calcium, magnesium, sodium, potassium, chloride, carbonates, and other ionic species. Consequently, it is not necessary to carefully monitor, as required, balance electrolyte concentrations in the patient's blood during prolonged treatment. However, as previously discussed, it is still possible to replenish electrolytes as needed at the physician's discretion by combining the present invention with conventional substitution and infusions fluids as known to those having ordinary skill in the art of physiology.

Specific non-limiting examples of non-ionic exchange resins suitable for use with the present invention include Amberlite™ XAD-7 HP and Amberchrom™ CG300-C. Amberlite™ is a group of polymeric synthetic resins made by the Rohm and Haas Company having a North American headquarters at 100 Independence Mall West Philadelphia, Pa. 19106-2399. Amberlite™ resins are available worldwide thorough a distributor network known to those skilled in the art. In one specific embodiment the present inventors have used Amberlite™ XAD-7 HP which is an aliphatic ester resin having an average surface area of approximately 500 $m^2/g$ and an average pore size of approximately 450 Angstroms and a mean diameter of approximately 560 µm.

Amberchrome™ CG300-G is a synthetic non-ionic exchange resin, also manufactured by Rohm and Haas, made from polystyrene divinyl benzene having an average surface area of approximately 700 $m^2/g$ with an average pore size of 300 Angstroms; mean particle diameter ranges from approximately 35 µm to approximately 120 µm.

However, whether the non-ionic exchange resins are used individually or in combination is not meant to be limiting, persons having ordinary skill in the art can easily select the exchange resin(s) best suited for a particular application. The factors that should be considered when selecting an appropriate exchange resin include the size, shape and charge of the molecule. Toxic molecules are general small and possess a few areas of high electron density but are known to possess carboxylic acid and amine residues that are easily polarizable and capable of hydrogen bonding. Larger macromolecules including cytokines, lymphokines and other toxic proteins have strong intermolecular forces suitable for removal using non-ionic resins that depend on van der Waal's forces to attract and bind molecules.

The activated carbon component of the toxin removal device of the present invention comprises elementary carbon in a graphite-like structure. It can be produced by heat treatment, or "activation," of raw materials such as, but not limited to, wood, coal, peat and coconuts. During the activation process, the unique internal pore structure is created, and it is this pore structure which provides activated carbon its outstanding adsorptive properties. Activated carbon is a carbonaceous adsorbent with a high internal porosity, and hence a large internal surface area. Commercial activated carbon grades have an internal surface area of 500 $m^2/g$ up to 1500 $m^2/g$. Two representative, non-limiting, examples of commercially available activated carbon include Carbomix™, available from Norit, Nederland B. V. Headoffice P.O. Box 105 3800 AC Amersfoort, The Netherlands and Ultracarbon™ available through Merck & Co., Inc., Whitehouse Station, N.J.

The toxin removal devices of the present invention generally comprise a combination of at least one ionic or non-ionic exchange resin and activated carbon. In one embodiment of the present invention a toxin removal device is a unitary structure having disposed therein at least one non-ionic resin in combination with activated charcoal. The unitary structure, such as a tubular member, may contain a homogenous mixture of the non-ionic exchange resin(s) and charcoal, or may have the charcoal and non-ionic exchange resin(s) separated into discrete chambers. In another embodiment of the present invention the toxin removal device may include a plurality of separate structures connected in series as depicted in FIG. 5. In yet another embodiment the toxin removal devices may include additional structures having cationic/anionic (or combinations thereof) ion exchange resins connected in series with the charcoal and non-ionic exchange resins.

In one embodiment of the present invention and referring to FIG. 1, a standard dual lumen hemodialysis catheter is required for performing treatments. Blood is removed through the arterial line of the hemodialysis catheter by the action of the continuous roller pump 104 at a relatively low blood flow rate of approximately 125 mL/min. The toxin-containing blood then enters a plasma filter 106. The plasma filter provides the continuous plasma filtration mode to generate plasma. This ensures that low, middle, and large molecular weight toxins are able to come into direct contact with the adsorbent filter while the cellular components of blood such as red blood cells (RBCs), platelets and leukocytes remain separate to avoid the drawbacks of direct hemoperfusion columns. Previous hemoperfusion columns were placed directly in the blood path, which allowed for activation or sequestration of platelets. The plasma filtrate that is generated is pumped by a second roller pump 116 at a rate of approximately 25 mL/min and passed through the toxin removing adsorbent column 120. In an embodiment of the present invention, the adsorptive toxin removal device contains activated uncoated coconut shell (carbon granules) charcoal and the non-ionic exchange resins Amberlite™ XAD-7HP and Amberchrom™ GC300C.

In another embodiment of the present invention, the adsorbent materials are coated with albumin before use, further increasing their biocompatibility. In this embodiment, albumin is coated directly on the adsorbent materials. Previously, activated carbon adsorbents were coated with cellulose to prevent platelet activation and to limit binding of beneficial plasma proteins. Cellulose, however, has the undesirable effect of decreasing total binding efficiency.

The present inventors have determined that pre-treating the adsorbent media with albumin during the priming process causes the adsorbent to be more biocompatible and decreases binding of beneficial plasma proteins. Priming refers to the process of flushing the extracorporeal system with biologically compatible fluids prior to the onset of the detoxification process. In yet another embodiment of the present invention, pre-treating the adsorbent media with albumin may also occur during the manufacturing process. In another embodiment, the adsorbent materials are used uncoated. The albumin coating does not contain a semi-permeable membrane.

Albumin suitable for coating the adsorbent materials of the present invention include, but are not limited to, human albumin and autologous albumin. In one embodiment, the albumin coating consists essentially of albumin and a pharmaceutically acceptable excipient or carrier in a physiologic solution. In another embodiment, the albumin coating consists essentially of albumin in a physiologic solution. Physiologic solutions compatible with the albumin coating include, but are not limited to, water and saline Lactated Ringer's solution and PLASMA-LYTE. In another embodiment, the adsorbent materials are coated with albumin such that the albumin coating is disposed directly onto the adsorbent materials.

In an embodiment of the present invention, the filtration replacement fluid 134 in FIG. 1 can be customized to the specific electrolyte and fluid needs of the patient. In CVVH, the CVVH system can rapidly remake the extracellular fluid in the image of the filtration replacement fluid. Higher concentrations of bicarbonate are occasionally used in patients with severe metabolic acidosis, but overcorrection can develop rapidly resulting in metabolic alkalosis. Precise fluid balance is one of the beneficial features of CVVH. The volume of filtration replacement fluid is adjusted each hour to yield the desired fluid balance. All fluids removed from the patient (ultrafiltrate, urine, gastric drainage, etc.) and all fluids administered to the patient except for the filtration replacement fluid are totaled each hour. The desired fluid balance (e.g. removal of 1000 mL/hr) is determined from clinical considerations.

In a specific embodiment of the present invention as depicted in FIG. 3, the extracorporeal circuit comprises two toxin removal device presented sequentially, the first toxin removal device 214 comprises an activated carbon column and the second toxin removal device 218 comprises non-ionic adsorption materials (activated carbon, Amberlite™ XAD-7 HP resin and Amberchrom™ CG300-C); 3-5 micron polypropylene depth filter pads attached to support structures 212, 216 and 220 to entrain the adsorbent material in the column; a commercially available plasma filter 206 with a 0.20-0.45 micron permeability; wherein the system is adapted to be used in conjunction with a commercially available continuous renal replacement therapy (CRRT) machine, such as, but not limited to the BBraum Diapact™. FIG. 3 depicts a patient 202 being in fluid communication with the toxin removal device of the present invention via a CRRT machine. A particle filter 222 such as one manufactured by Minntech (FiberFlo™ Capsule Water Filter, for example) is used downstream from the toxin removal device to filter any small particles prior to return to the patient.

A standard dual lumen hemodialysis catheter is required for performing treatments. Blood is removed through the arterial line of the hemodialysis catheter by the action of the continuous roller pump 204 at a relatively low blood flow rate of approximately 125 mL/min. The toxin-containing blood then enters a plasma filtration step 206. The plasma filter provides the continuous plasma filtration mode to generate plasma. This ensures that low, middle, and large molecular weight toxins are able to come into direct contact with the toxin removal device. In the next step, the cellular components of blood such as RBCs, platelets and leukocytes remain separate to avoid the drawbacks of direct hemoperfusion columns. Previous hemoperfusion columns were placed directly in the blood path, which allowed for activation and sequestration of platelets. The extracorporeal system of the present invention avoids these undesirable effects. The plasma filtrate that is generated is pumped by a second roller pump 208 at a rate of approximately 25 mL/min and passed through the toxin removal devices 214 and 218 containing activated uncoated coconut shell (carbon granules) charcoal (100 gm), and the non-ionic resins Amberlite™ XAD-7HP (30 gm) and Amberchrom™ GC300C (35 gm). During the priming phase of preparation for toxin removal treatment, albumin in the priming solution coats the adsorbent materials in the toxin removal device(s) further increasing their biocompatibility.

The detoxified plasma is then rejoined to the blood path 224 and is subsequently returned to the patient 202 through the venous line of the hemodialysis catheter. A commercially available hemoconcentrator 226 [Minntech HPH 400TS™] may be added to the circuit to enable ultrafiltration fluid removal, at the discretion of the treating physician, depending on patient needs.

The safety of extracorporeal detoxification utilizing the commercially available B|BRAUN DIAPACT™ CRRT machine in Plasma Adsorption/Perfusion (PAP) mode has been demonstrated. In one embodiment of the present invention the B|BRAUN DIAPACT™ CRRT machine in PAP mode is utilized in accordance with it's approved labeling including the use of standard PAP mode tubing, hardware, software and safety settings. The B|BRAUN DIAPACT™ CRRT machine in PAP mode is currently used clinically with the Asahi Medical Co. PlasmaFlo plasma filter and the Asahi CH-350 charcoal hemoperfusion column. The safety and efficacy of the substitution of the present invention for the Asahi charcoal column in an extracorporeal circuit controlled with the B|BRAUN DIAPACT™ CRRT machine in PAP mode will be demonstrated by ongoing clinical studies.

There are significant advantages to the present invention over currently used renal dialysis techniques. First, the use of an adsorption column allows for the targeted removal of both protein-bound and soluble toxins associated with sepsis and renal failure that cannot be removed or removed efficiently, using standard renal dialysis. Secondly, the use of combined ZBUF and CVVH facilitates the removal of waste materials and the stabilization of electrolytes as well as the simultaneous controlled removal of excess plasma water. Additionally, the composition of the ZBUF replacement fluid can be customized to meet patient physiologic requirements.

EXAMPLES

The following examples are not intended as limitations. Rather they demonstrate illustrative embodiments of the present invention.

Example 1

In Vitro Clearance Capabilities of the Adsorptive Toxin Removal Device

To demonstrate the efficacy of the adsorptive toxin removal device of the present invention (FIG. 5), human plasma spiked with bilirubin (20 mg/dL), urea nitrogen (50 mg/dL), and creatinine (5 mg/dL) was circulated through a closed system with separate columns containing activated charcoal, Amberlite™ XAD-7HP, and Amberchrom™ GC 300C (referred to herein individually as "sorbants") for 6 hours. The sorbants demonstrated varying effectiveness in clearing bilirubin, urea nitrogen and creatinine: activated charcoal (36 gm) decreased the levels of bilirubin by 49.5%, urea nitrogen 24.7%, and creatinine 97.9% of baseline values; Amberlite™ XAD-7HP (31 gm) decreased the levels of bilirubin by 34.6%, urea nitrogen 11.2%, and creatinine 9.0% of baseline values; Amberchrom™ GC300C decreased the levels of bilirubin by 95.7%, urea nitrogen 11.2%, and creatinine 10.1% of baseline values. Associated with these clearances was a modest 15-20% decrease in plasma albumin and total protein concentrations.

Figure 6A:
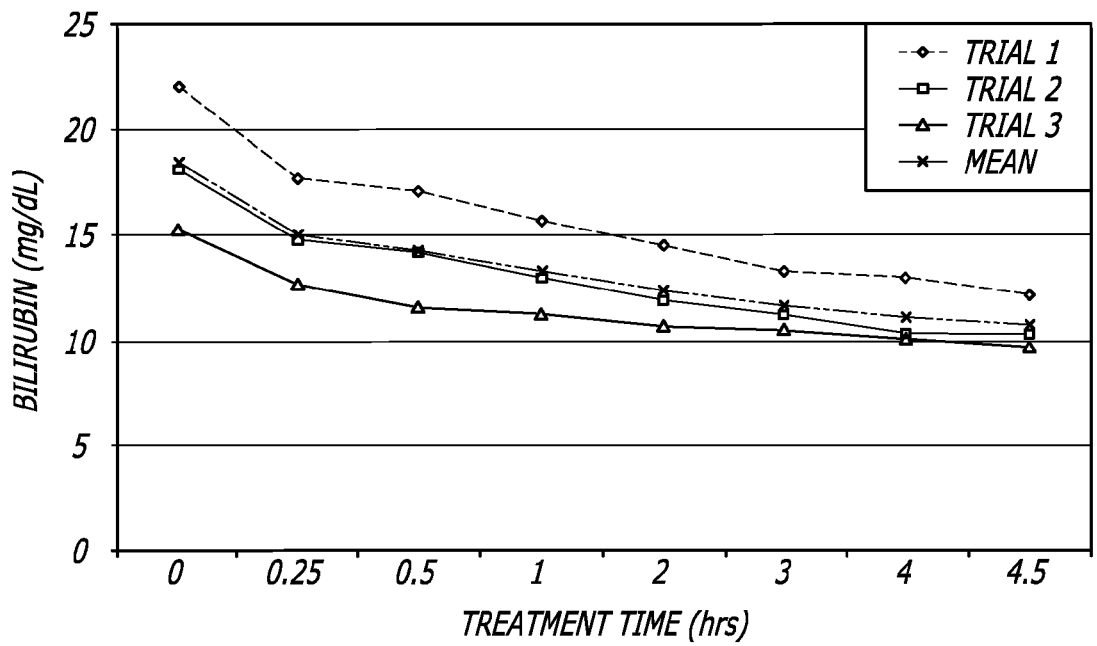
FIG. 6A-C graphically depicts the efficacy of the adsorptive toxin removal device of the present invention in decreasing initial blood levels of bilirubin (FIG. 6A), urea nitrogen (FIG. 6B) and creatinine (FIG. 6C).
Figure 6B:
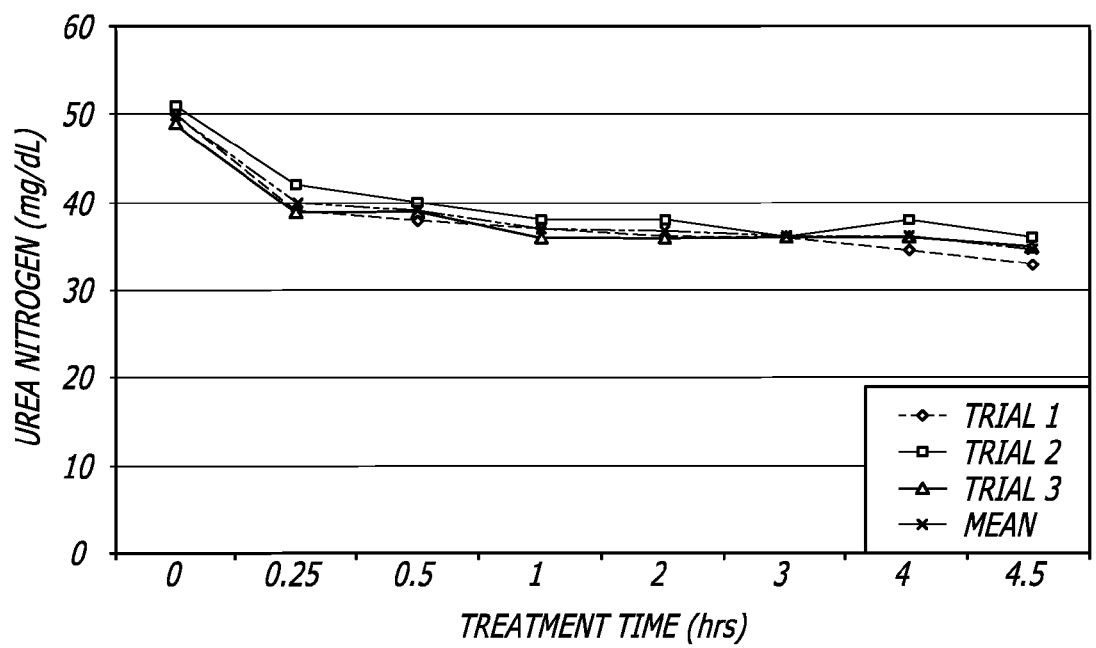
Figure 6C:
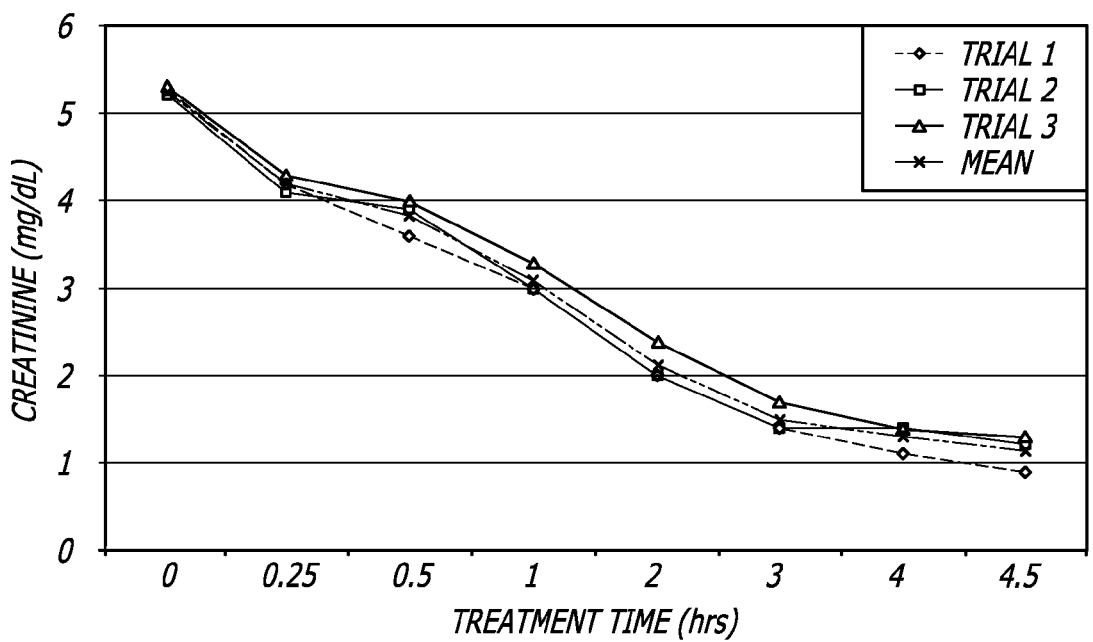
Figure 7:
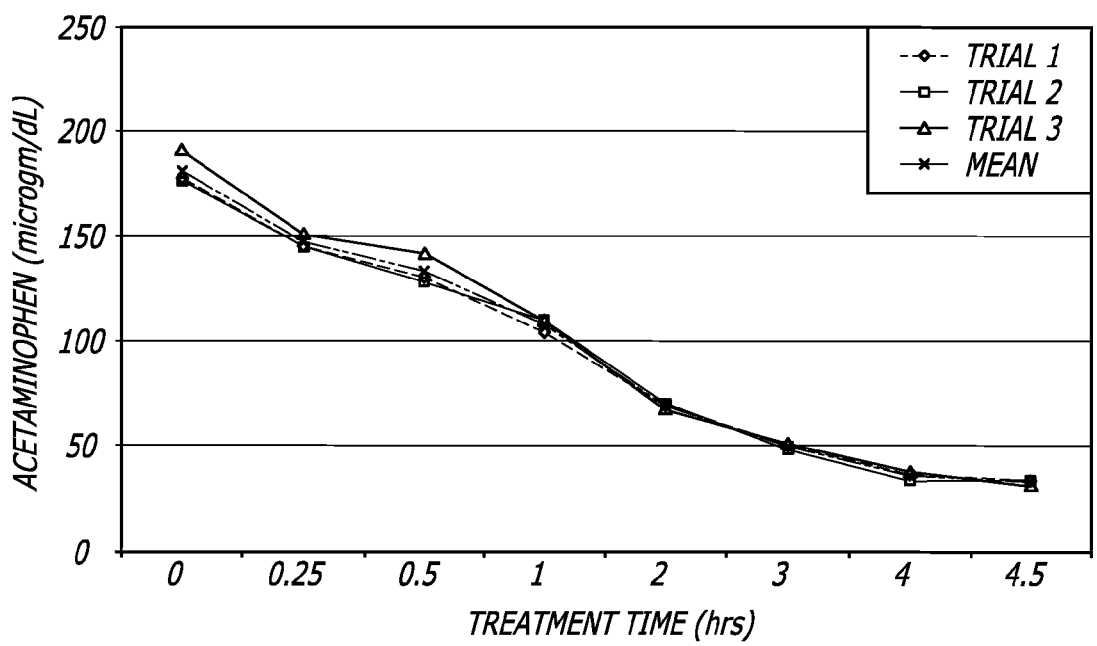
FIG. 7 graphically depicts the efficacy of the adsorptive toxin removal device of the present invention in decreasing blood acetaminophen concentration.

A separate series of in vitro experiments was carried out utilizing the adsorptive toxin removal device of the present invention containing 100 gm activated uncoated coconut shell granule charcoal, 35 gm Amberlite™ XAD-7HP, and 35 gm Amberchrom™ GC300C (dry weights) (the HLM-100 adsorptive column). Heparinized human plasma was spiked with bilirubin, urea nitrogen, and creatinine at approximate initial concentrations of 20 mg/dL, 50 mg/dL, and 5 mg/dL, respectively. The adsorptive toxin removal device of the present invention decreased initial bilirubin, urea nitrogen, and creatinine levels by 41.4%, 30.7%, 78.3% respectively (see Table 1 and FIGS. 6A-C). In addition to these endogenous toxins, acetaminophen was added to the plasma at an initial concentration of approximately 175-200 micrograms/mL. The adsorptive toxin removal device decreased the initial acetaminophen concentration by 82.4% (see FIG. 7). There was a modest 10-15% decrease in total protein and albumin, in addition to a 25-30% fibrinogen decline with this embodiment of the present invention.

TABLE 1

In Vitro Investigation of the HLM-100 Adsorptive Toxin Removal Device

| Toxins | Percent Decrease in Initial Toxin Levels (Percent ± SD) |
|---|---|
| Endogenous Toxins | |
| bilirubin | 41.4 ± 4.2 |
| urea nitrogen | 30.7 ± 2.9 |
| creatinine | 78.3 ± 3.8 |
| Exogenous Toxin | |
| acetaminophen | 82.4 ± 1.3 |

This in vitro data confirms the ability of the adsorptive toxin removal device of the present invention to effectively remove toxins associated with acute liver failure and acute-on-chronic liver failure. The clearance of bilirubin also indicates the clearance of bile acids, which are toxic to hepatocytes, impair CNS function and the immune response to infection. The removal of acetaminophen confirms the ability of the adsorptive toxin removal device of the present invention to remove exogenous toxins.

Example 2

Safety Testing of the Adsorptive Toxin Removal Device

The safety of the adsorptive toxin removal device of the present invention was also investigated in a canine extracorporeal circulation model involving eight approximately 55 pound mongrel dogs. The purpose of the safety testing was to demonstrate that the adsorptive toxin removal device does not remove beneficial plasma proteins or electrolytes. The test results obtained demonstrated that treatments using the adsorptive toxin removal device in conjunction with a commercially available kidney dialysis system, the Diapact™ continuous renal replacement therapy (CRRT) system (B|BRAUN Medical Inc., Bethlehem, Pa.) in plasma adsorption/perfusion (PAP) mode, were safe and well tolerated without detrimental hemodynamic effects or biocompatibility concerns.

Testing involved canine model extracorporeal circulation with the Diapact™ CRRT system in PAP mode was performed for a lead-in hour to determine the effects of the extracorporeal circuit without inclusion of plasma filtration and the HLM-100 adsorptive toxin removal device (blood loop). The plasma flow pump was then initiated with the adsorptive toxin removal device (adsorbent column) included into the plasma flow path of the extracorporeal circulation (plasma loop) for an additional four hours (total of 6 liters of plasma processed by adsorptive toxin removal device).

Figure 8A:
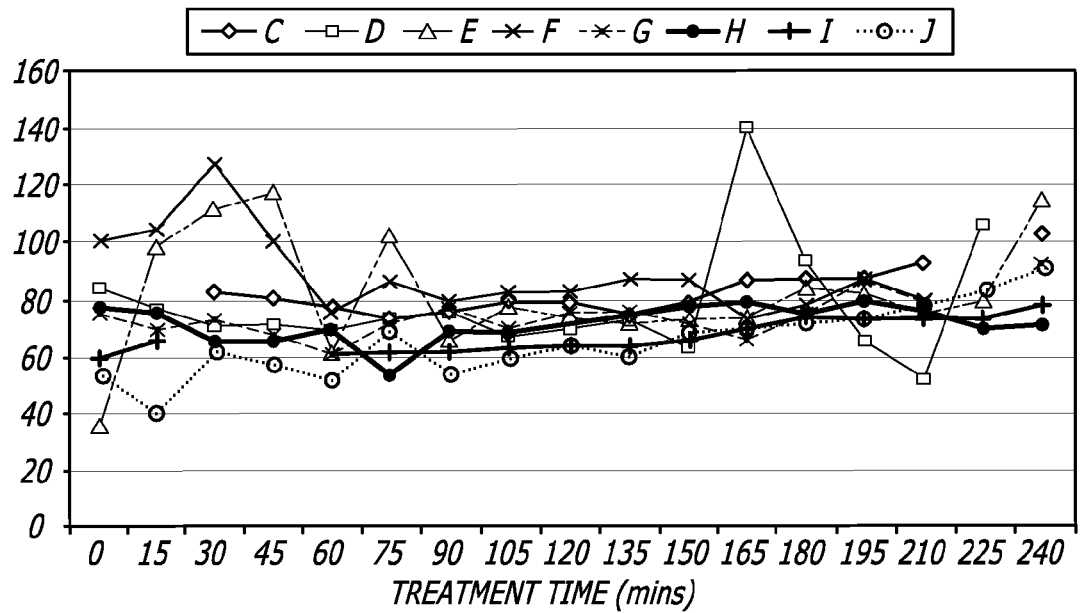
FIG. 8A-F graphically depicts testing demonstrating that inclusion of the adsorptive toxin removal device of the present invention into an extracorporeal circuit did not result in evidence of hemodynamic instability (FIG. 8A), hemolysis (FIG. 8B), thrombocytopenia (FIG. 8C), leucopenia (FIG. 8D), or nonspecific loss of fibrinogen (FIG. 8E) or albumin (FIG. 8F) (Animals identified as C-J; ET=End of Treatment values)
Figure 8B:
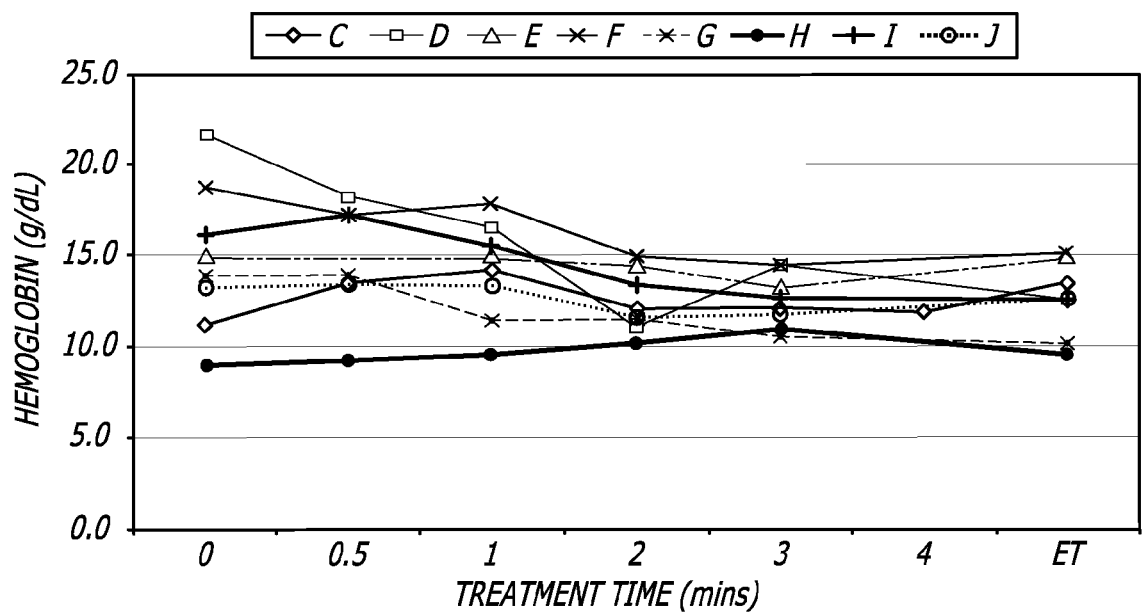
Figure 8C:
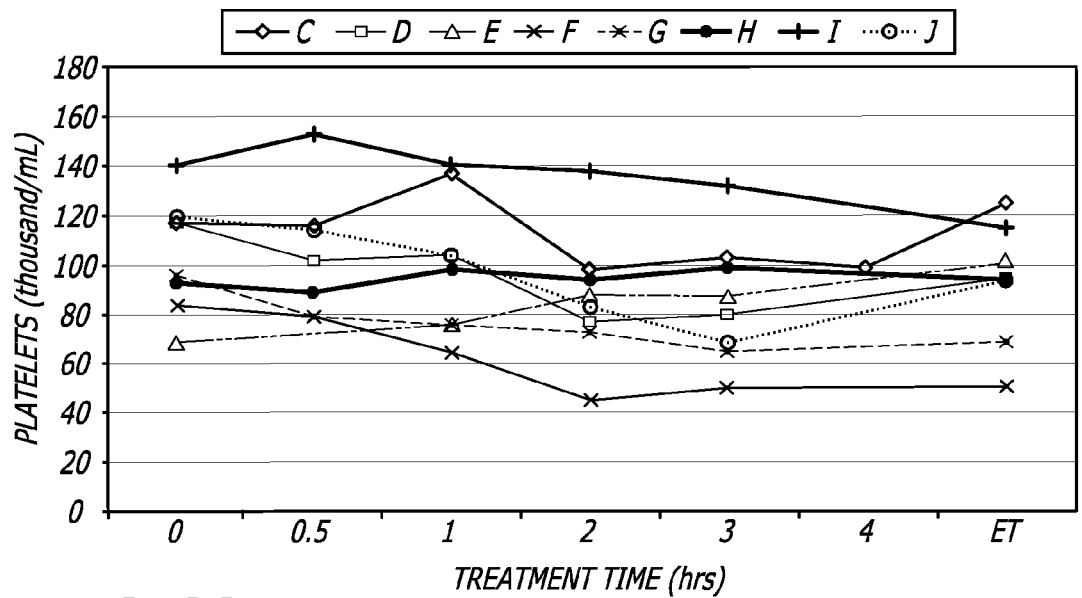
Figure 8D:
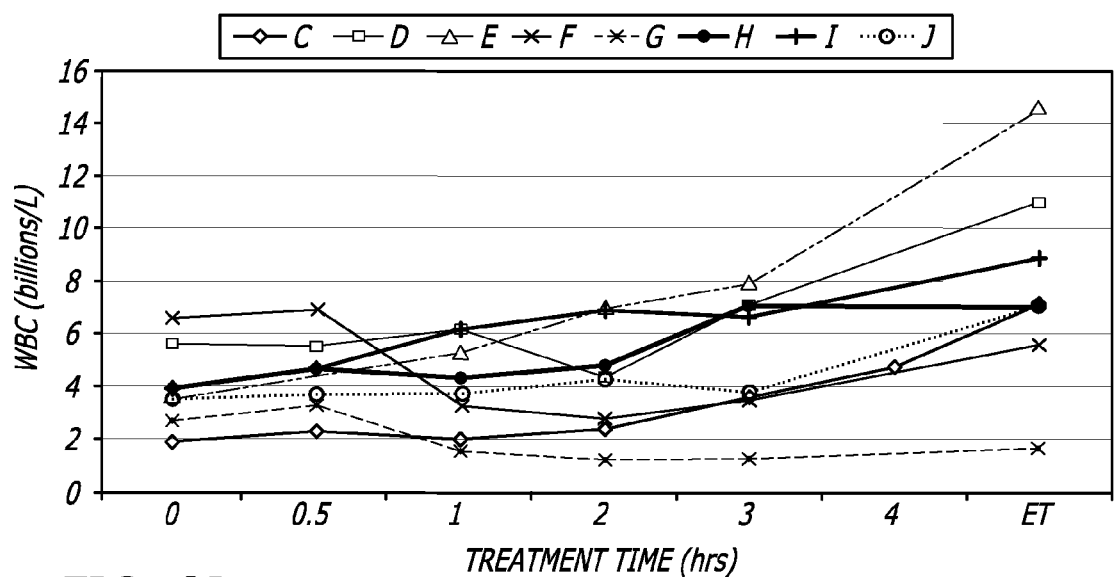
Figure 8E:
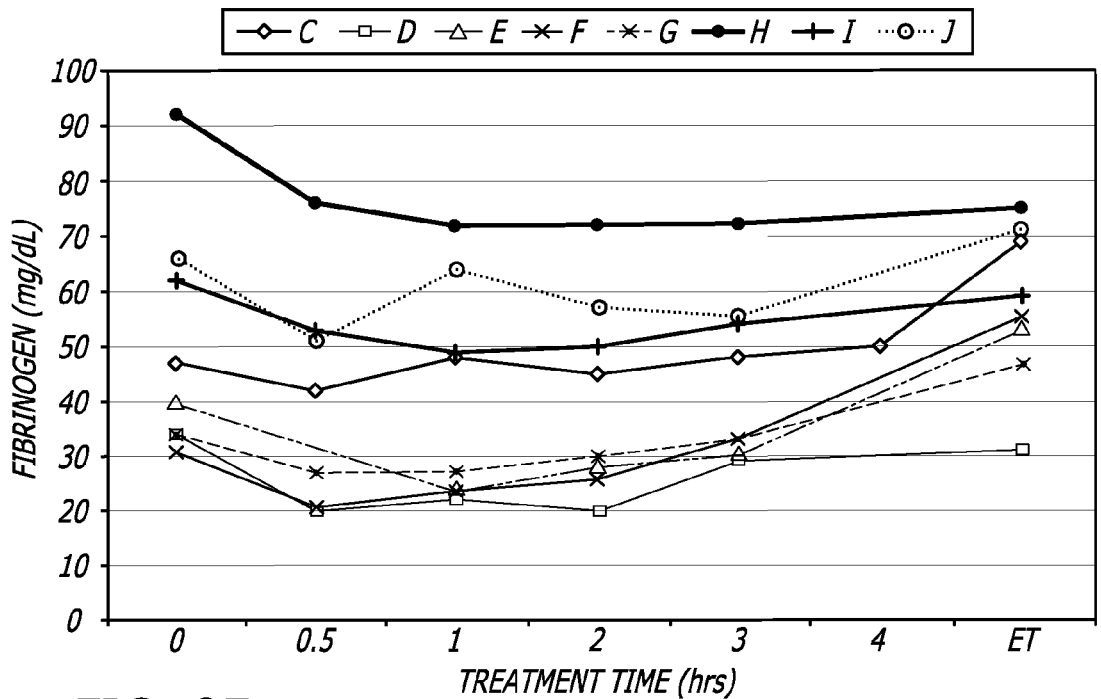
Figure 8F:
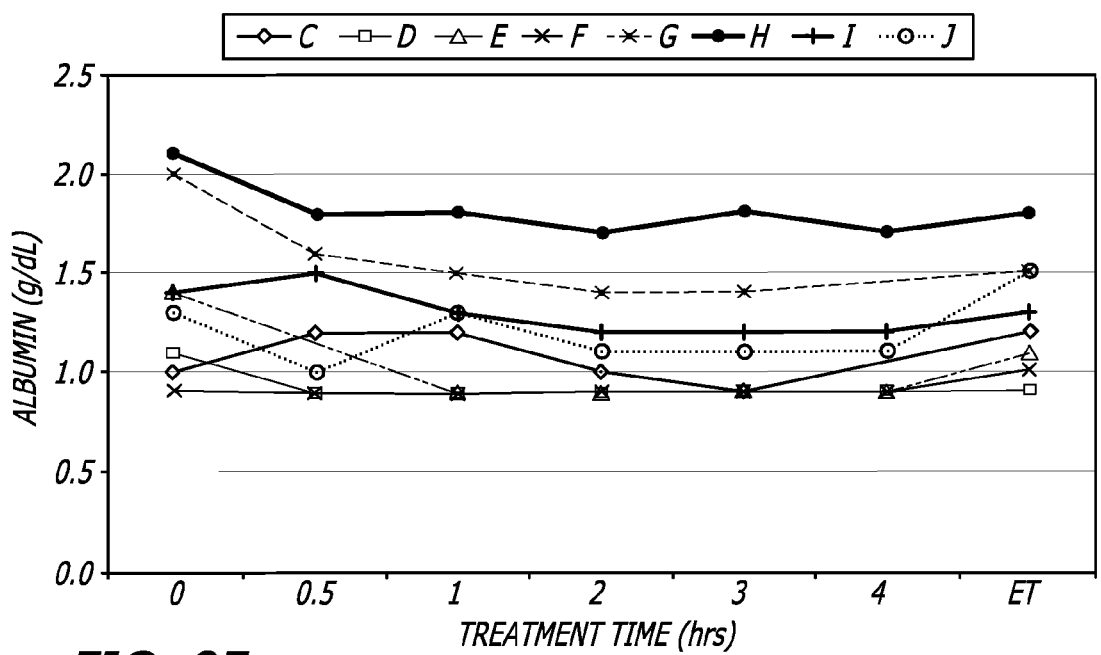

Inclusion of the HLM-100 adsorbent column into an extracorporeal circuit did not result in evidence of hemodynamic instability (FIG. 8A), hemolysis (FIG. 8B), thrombocytopenia (FIG. 8C), leucopenia (FIG. 8D), or nonspecific loss of fibrinogen (FIG. 8E) or albumin (FIG. 8F) (Animals identified as C-J; ET=End of Treatment values). Over the course of the four hours of extracorporeal circulation with the adsorptive column there was an increase in mean arterial pressure. Comparison of the various parameters pre- and post-inclusion of the HLM-100 adsorbent column confirmed that the inclusion of the adsorbent column was safe (see Table 2). There was also no evidence of adsorption column-related electrolyte abnormalities or consumption of clotting factors. There were minor anticoagulation-related bleeding noted at the cut down sites for the hemodialysis catheter in addition to the invasive hemodynamic monitoring catheters (pulmonary artery catheter and arterial catheter).

TABLE 2

A comparison of the effect of the toxin removal device of the present invention inclusion into an extracorporeal circuit in a canine model prior to and following conclusion of 4 hours of treatment.

| | Prior to HLM-100 column inclusion in circuit | Following HLM-100 column inclusion in circuit for 4 hr | p value |
|---|---|---|---|
| Mean Arterial Pressure (mmHg) | 71 ± 20 | 92 ± 16 | <0.05 |
| Hemoglobin (g/dL) | 14.8 ± 4.0 | 12.6 ± 2.0 | NS |
| Platelet (Thousand/mL) | 104 ± 23 | 93 ± 24 | NS |
| WBC (Thousand/mL) | 4.0 ± 1.5 | 7.9 ± 3.8 | <0.05 |
| Serum Fibrinogen (mg/dL) | 52 ± 22 | 58 ± 14 | NS |
| Serum Albumin (g/dL) | 1.4 ± 0.4 | 1.3 ± 0.4 | NS |

There are significant advantages to this technique and technology over conventional renal dialysis. The use of an adsorption column allows for the targeted removal of both protein bound and soluble toxins associated with sepsis and renal failure that cannot be removed or removed efficiently, using standard dialysis techniques. In addition, the use of combined zero-balance ultrafiltration (ZBUF) and continuous venovenous hemofiltration (CVVH) facilitated the removal of waste materials and the stabilization of electrolytes as well as the simultaneous controlled removal of excess plasma water. And, the composition of the ZBUF replacement fluid can be customized to meet patient physiologic requirements.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on those embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are individually incorporated by reference herein in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An extracorporeal system for the removal of cytokines and toxins from plasma and to balance plasma water comprising:
   a plasma filter for separating plasma from blood, and
   an adsorption device for removing cytokines and toxins from the plasma;
   wherein said adsorption device comprises two or more adsorbents selected from the group consisting of activated carbon, non-ionic exchange resin and ion exchange resin, said adsorbents are coated with human albumin prior to use in the absence of a semi-permeable membrane, and wherein binding of cytokines and toxins to said adsorbents is not increased as a result of said albumin coating.

2. The extracorporeal system of claim 1 wherein said plasma filter has a molecular weight cutoff greater than 0.2 microns.

3. The extracorporeal system of claim 1 further comprising a hemofilter for removing small molecules from the plasma and balancing plasma water.

4. The extracorporeal system of claim 1 wherein said activated carbon comprises uncoated coconut shell granule charcoal.

5. The extracorporeal system of claim 1 wherein said activated carbon comprises uncoated organic granule charcoal or uncoated synthetic carbon.

6. The extracorporeal system of claim 1 wherein said adsorbent is at least one ion exchange resin.

7. The extracorporeal system of claim 1 wherein said adsorbent is at least one non-ionic exchange resin.

8. The extracorporeal system of claim 7 wherein said at least one non-ionic exchange resin is selected from the group consisting of non-ionic aliphatic ester resins, non-ionic polystyrene divinyl benzene resins and other non-biologic adsorptive resins.

9. The extracorporeal system of claim 8 wherein at least one of said non-ionic aliphatic ester resins has an average surface area of approximately 500 $m^2/g$ and an average pore size of approximately 450 Angstroms and a mean particle diameter of 560 μm.

10. The extracorporeal system of claim 8 wherein at least one of said non-ionic polystyrene divinyl benzene resins has an average surface area of approximately 700 $m^2/g$ with an average pore size of 300 Angstroms and a mean particle diameter from approximately 35 µm to approximately 120 µm.

11. The extracorporeal system of claim 8 wherein at least one of said non-ionic polystyrene divinyl benzene resins has an average surface area of approximately 600 m$^2$/g with an average pore size of 300 Angstroms and a mean particle diameter from approximately 300 µm to approximately 500 µm.

12. The extracorporeal system of claim 1 further comprising at least one particle filter downstream of said adsorption device in said extracorporeal system.

13. The extracorporeal system of claim 1 wherein said albumin coating consists essentially of albumin and a physiologic solution.

14. The extracorporeal system of claim 13 wherein said albumin is autologous human albumin.

15. An extracorporeal system for the removal of cytokines and toxins from plasma and to balance plasma water comprising:
  a plasma filter for separating plasma from blood, and
  an adsorption device for removing cytokines and toxins from the plasma;
  wherein said adsorption device comprises two or more adsorbents selected from the group consisting of activated carbon, non-ionic exchange resin and ion exchange resin and wherein said adsorbents are coated with human albumin prior to use, said albumin coating consisting essentially of albumin and a physiologic solution and said albumin coating does not comprise a semi-permeable membrane,
  wherein binding of cytokines and toxins to said adsorbents is not increased as a result of said albumin coating.

16. A method for removing toxins from blood comprising:
  circulating the venous blood of a patient through an extracorporeal circuit having an adsorptive toxin removal device disposed therein wherein said toxin removal device comprises activated carbon and two or more non-ionic resins wherein said activated carbon and said two or more non-ionic resins are coated with human albumin in the absence of a semi-permeable membrane, wherein binding of cytokines and toxins to said adsorbents is not increased as a result of said albumin coating.

17. The method according to claim 16 further comprising a hemofilter.

18. A method for treating a disease or disorder in a mammal comprising:
  circulating the venous blood of a patient through an extracorporeal circuit having an adsorptive toxin removal device disposed therein wherein said adsorptive toxin removal device comprises activated carbon and two or more non-ionic resins wherein said activated carbon and said two or more non-ionic resins are coated with human albumin in the absence of a semi-permeable membrane, wherein binding of cytokines and toxins to said adsorbents is not increased as a result of said albumin coating, and
  wherein said extracorporeal circuit optionally further comprises a hemofilter.

19. The method according to claim 18 wherein said disease or disorder is sepsis.

20. The method according to claim 18 wherein said disease or disorder is renal failure.

21. The method according to claim 18 wherein said disease or disorder is liver failure.

* * * * *